(12) United States Patent
Veronesi et al.

(10) Patent No.: US 6,251,429 B1
(45) Date of Patent: Jun. 26, 2001

(54) PROGRAMMED RELEASE AMBROXOL—HCL DOSAGE FORMS

(75) Inventors: Paolo Alberto Veronesi; Anna Maria Veronesi, both of Milan (IT)

(73) Assignee: Therapicon slr, Milan (IT)

( * ) Notice: Subject to any disclaimer, the term of this patent is extended or adjusted under 35 U.S.C. 154(b) by 0 days.

(21) Appl. No.: 08/380,218

(22) Filed: Jan. 30, 1995

Related U.S. Application Data

(63) Continuation of application No. 07/989,558, filed on Dec. 11, 1992.

(30) Foreign Application Priority Data

Dec. 11, 1991 (IT) .............................. MI91A3318

(51) Int. Cl.[7] .............................. A61K 9/16; A61K 9/50; A61K 31/135
(52) U.S. Cl. .................. 424/458; 424/461; 424/462; 424/490; 424/494; 424/495; 424/497
(58) Field of Search .................. 424/490, 494, 424/495, 497, 458, 461, 462

(56) References Cited

U.S. PATENT DOCUMENTS

| | | | |
|---|---|---|---|
| 4,957,745 | * | 9/1990 | Jonsson et al. ............ 424/494 |
| 4,996,047 | * | 2/1991 | Kelleher et al. ............ 424/486 |
| 5,026,560 | * | 6/1991 | Makino et al. ............ 424/494 |
| 5,084,287 | * | 1/1992 | Ghebre-Sellassie et al. ...... 424/494 |
| 5,133,974 | * | 7/1992 | Paradissis et al. ............ 424/494 |
| 5,167,964 | * | 12/1992 | Muhammad et al. ............ 424/494 |
| 5,213,811 | * | 5/1993 | Frisbee et al. ............ 424/494 |
| 5,376,386 | * | 12/1994 | Ganderton et al. ............ 424/499 |
| 6,120,802 | * | 9/2000 | Breitenbach et al. ............ 424/464 |

FOREIGN PATENT DOCUMENTS

| | | | |
|---|---|---|---|
| 3943242 A1 | * | 6/1990 | (DE) . |
| 125634 A1 | * | 11/1984 | (EP) . |
| 208144 A1 | * | 1/1987 | (EP) . |
| 9806385 | * | 2/1998 | (WO) . |

* cited by examiner

Primary Examiner—Robert H. Harrison
(74) Attorney, Agent, or Firm—Burns, Doane, Swecker & Mathis, L.L.P.

(57) ABSTRACT

Programmed-release ambroxol·HCl pharmaceutical dosage forms, adopted to maintain a therapeutically effective plasma level thereof for about 24 hours, comprise a plurality of inert core microgranules of a variety of particle sizes ranging from 0.3 to 1.2 mm, such inert core microgranules being coated with alternating microlayers of (1) micronized ambroxol hydrochloride active agent and (2) delayed-release film material, such coated microgranules including an external microlayer of delayed-release film material, and such coated mi.crogranules having particle sizes ranging from 0.6 to 1.5 mm.

13 Claims, 1 Drawing Sheet

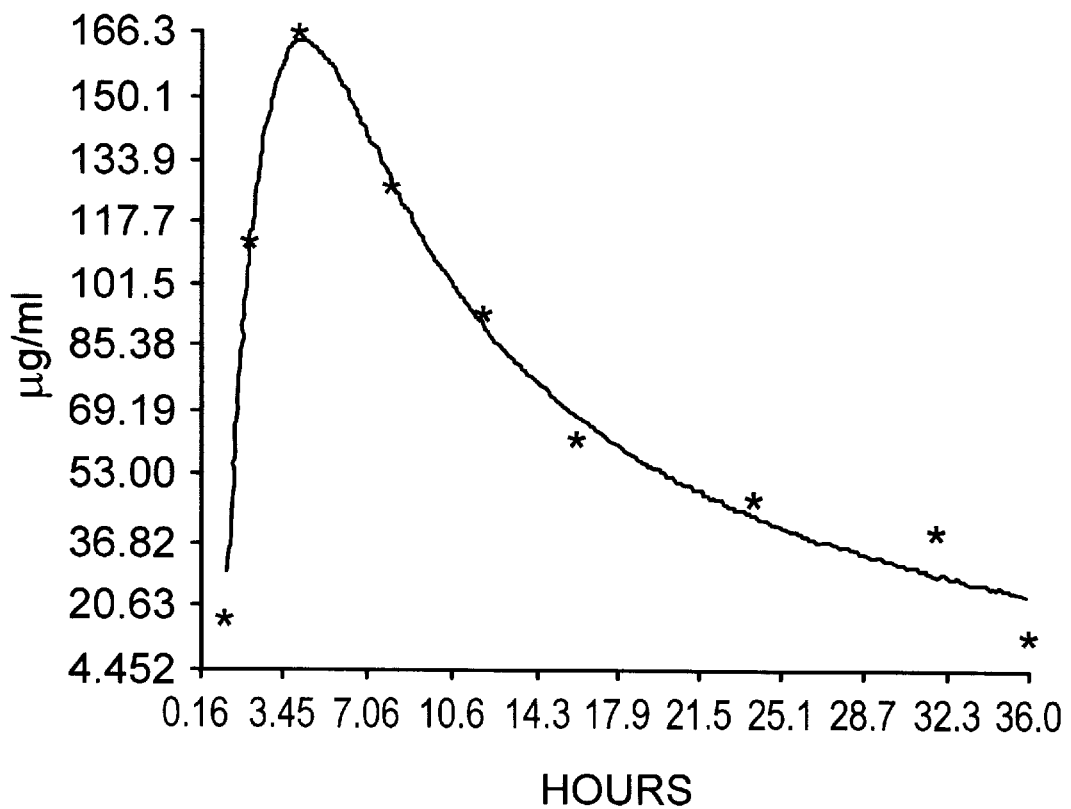
FIGURE

PROGRAMMED RELEASE AMBROXOL— HCL DOSAGE FORMS

This application is a continuation, of application Ser. No. 07/989,558, filed Dec. 11, 1992.

BACKGROUND OF THE INVENTION

1. Field of the Invention

The present invention relates to unique programmed-release pharmaceutical dosage forms comprising ambroxol hydrochloride.

2. Description of the Prior Art

Ambroxol, 4-[[(2-amino-3,5-dibromophenyl)methyl]amino]cyclohexanol or N-(trans-p-hydroxycylohexyl)-(2-amino-3,5-dibromobenzyl)amine, is a known compound (compare, for example, U.S. Pat. No. 3,536,713). Ambroxol hydrochloride too is known to this art, as is the pharmaceutical activity thereof. Ambroxol·HCl, for example, is a safe and effective expectorant. Nonetheless, it possesses a relatively short biological half-life and, therefore, it typically must be administered at least three times a day in order to elicit its full activity.

Thus, need continues to exist in this art for an improved dosage form of ambroxol·HCl that will permit a decrease in the number of administrations, to not only reduce the burden on the patient but also to increase his compliance, thus providing greater therapeutic benefits.

SUMMARY OF THE INVENTION

Accordingly, a major object of the present invention is the provision of improved programmed-release ambroxol·HCl dosage forms that slowly release its active ingredient, such that it will maintain therapeutically effective levels of the active drug in the bloodstream for a prolonged period of time.

Briefly, the present invention features a pharmaceutically acceptable dosage form of ambroxol hydrochloride that will slowly and programmedly release almost the totality of its content of active ambroxol·HCl over a time period of about 16 hours, in order to prolong the plasma levels thereof for almost 24 hours.

DETAILED DESCRIPTION OF THE PREFERRED EMBODIMENTS OF THE INVENTION

More particularly according to the present invention, it will be appreciated that certain techniques have heretofore been proposed to this art for preparing slow-release pharmaceutical compositions containing ambroxol hydrochloride which are capable of retaining the concentrations of active ingredient in the blood for a somewhat prolonged period of time. Such dosage forms, however, suffer from the disadvantages that neither the minimum quantity of ambroxol hydrochloride is released therefrom "in vitro" after fixed intervals (programmed-release profile with indication of the minimum amount to be released at fixed intervals), nor are they immune to the influence and possible variations of the preparation during the aging or storage thereof (stability of the programmed-release rate of the preparation over time).

The unique dosage forms of this invention are conspicuously devoid of the above disadvantages and drawbacks and are produced via a seriatim procedure that first comprises the preparation of inert microgranules, preferably starch and sugar microgranules. Selection of the microgranules is next carried out by sieving them through a sieve opening ranging from 0.3 mm to 1.2 mm. The ambroxol hydrochloride, characteristically in admixture with talc or with other supports, for example aluminum or magnesium silicates or lactose, is then micronized until a mixture having particle sizes ranging from 1 to 150 microns is obtained. Application onto the inert microgranules of multiple, alternate microlayers of this powder mixture and of the delayed-release film-forming agent, which is advantageously a polyvinylpyrrolidone, polyvinylpyrrolidone/shellac mixture or shellac itself, is accomplished by spraying or atomizing, via a seriatim procedure, suitable aliquots of the suspensions or solutions thereof and then consolidating each microlayer to dryness, with air or without air.

The solvents for the film-formers are advantageously aqueous or mixtures of alcohol or of acetone.

The concentration of ambroxol hydrochloride in the microgranules according to the invention advantageously ranges from 100 to 500 mg per gram. The ambroxol hydrochloride is thus incorporated as microlayers on the granules, and same are coated with a delayed-release film-coating material, notably shellac, an acrylic resin (e.g., that marketed under the trademark Eudragit by Röhm Pharma, Germany) hydroxypropyl methylcellulose, ethylcellulose or derivatives thereof, or mixtures of the above materials dissolved in organic solvents, e.g., alcohol, acetone or others, or in aqueous mixtures with organic solvents;

talc is also added during this final operation.

Thus produced is a programmed-release ambroxol·HCl pharmaceutical dosage form, comprising a plurality of inert core microgranules of a variety of particle sizes ranging from 0.3 to 1.2 mm, such inert core microgranules being coated with alternating microlayers of (1) micronized ambroxol hydrochloride active agent and (2) delayed-release film material, such coated microgranules including an external microlayer of delayed-release film material, and such coated microgranules having particle sizes ranging from 0.6 to 1.5 mm.

The manufactured batches are subjected to a dissolution test to determine the release rate profile by means of the apparatus recommended by U.S.P. XXII, Model I at 100 revolutions per minute, using 900 ml of water as the immersion liquid. They are formulated to strictly satisfy the following release rate limits, also characterizing the present invention:

| | |
|---|---|
| 01st hour | 20%–40% |
| 08th hour | 55%–75% |
| 16th hour | >75% |

The programmed-release microgranules of ambroxol hydrochloride may then be easily administered in the recommended doses, as they are more conveniently packaged in unitary daily dosage amounts in primary dosage forms composed of hard gelatin capsules.

In order to further illustrate the present invention and the advantages thereof, the following specific examples are given, it being understood that same are intended only as illustrative and in nowise limitative.

EXAMPLE 1

Inert microgranules of sugar and starch were prepared from 500 g of sugar and from 500 g of an aqueous solution of sugar and starch (1:1) and the film-coating thereof was demonstrated (two experiments).

400 g of an aqueous solution of sugar and starch were injected into a rotating pan containing 500 g of sugar and inert microgranules almost spherical in shape were produced. These inert microgranules were dried for 24 hours at 50° C. and sieved to a size of from 0.3 to 1.2 mm.

500 g of the neutral microgranules thus produced were added to 190 g of a micronized mixture of ambroxol hydrochloride and starch (98:2) having a particle size of about 10 microns, and incorporated into the mixture using a 20% solution of shellac (80%) and polyvinylpyrrolidone (20%) in isopropanol by means of an airless spraying (atomizing) system (about 100 g of solution).

During this step, the following parameters were maintained under constant control:

(a) The size of the particles at values ranging from 1 to 150 microns by conducing two tests therefor during the process;
(b) The amount of micronized ambroxol hydrochloride to be incorporated was controlled at from 100 to 500 mg/g of final product;
(c) The amounts and the proportions of the shellac and polyvinylpyrrolidone were varied, as required;
(d) For a better modulation of the programmed-release profile, another delayed-release film-forming agent could be added to the shellac, or substituted therefor.

EXAMPLE 2

Release Rates:

The products of the two experiments of Example 1 were tested according to the U.S.P. XXII system, Model I at 100 revolutions per minute, using 900 ml of water as the immersion liquid, and the following results reported in Table I were obtained:

TABLE I

| | Specifications | Release profile obtained |
|---|---|---|
| Product of Experiment 1 of Example 1 | | |
| 1st hour | 20–40% | 29% |
| 8th hour | 55–75% | 72% |
| 16th hour | >75% | 89% |
| Product of Experiment 2 of Example 1 | | |
| 1st hour | 20–40% | 28% |
| 8th hour | 55–75% | 72% |
| 16th hour | >75% | 91% |

EXAMPLE 3

Stability tests were conducted to confirm the liberation or release profile and other basic parameters of the programmed-release microgranules of the two experiments of Example 1.

Five samples of 5 grams each of the two products from the experiments of Example 1 were sealed in amber glass bottles with plastic screw-caps and were stored at 250 and 50° C., respectively, for a consecutive period of 5 years and tested at the end of each interval of one year; the results reported in Table II were obtained:

TABLE II

| Temperature 25° C. | | Intervals (Years) | | | | |
|---|---|---|---|---|---|---|
| Parameters | Specifications | 1st | 2nd | 3rd | 4th | 5th |
| Product of Experiment 1 of Example 1: | | | | | | |
| Appearance | Conform | Conf. | Conf. | Conf. | Conf. | Conf. |
| Assay (potency) as % ambroxol·HCl | 20–28% | 24% | 24% | 25% | 24% | 24% |
| Release profile: | | | | | | |
| 1st hour | 20–40% | 29% | 30% | 31% | 32% | 31% |
| 8th hour | 55–75% | 73% | 73% | 73% | 73% | 72% |
| 16th hour | >75% | 88% | 89% | 88% | 89% | 90% |
| Product of Experiment 2 of Example 1: | | | | | | |
| Appearance | Conform | Conf. | Conf. | Conf. | Conf. | Conf. |
| Assay (potency) as % ambroxol·HCl | 20–28% | 24% | 24% | 24% | 25% | 24% |
| Release profile: | | | | | | |
| 1st hour | 20–40% | 29% | 29% | 29% | 30% | 29% |
| 8th hour | 55–75% | 73% | 73% | 72% | 73% | 72% |
| 16th hour | >75% | 90% | 88% | 89% | 89% | 91% |
| Product of Experiment 1 of Example 2: | | | | | | |
| Appearance | Conform | Conf. | Conf. | Conf. | Conf. | Conf. |
| Assay (potency) as % ambroxol·HCl | 20–28% | 25% | 25% | 25% | 24% | 25% |
| Release profile: | | | | | | |
| 1st hour | 20–40% | 29% | 29% | 30% | 31% | 31% |
| 8th hour | 55–75% | 72% | 71% | 71% | 72% | 72% |
| 16th hour | >75% | 92% | 90% | 92% | 91% | 90% |
| Product of Experiment 2 of Example 2: | | | | | | |
| Appearance | Conform | Conf. | Conf. | Conf. | Conf. | Conf. |
| Assay (potency) as % ambroxol·HCl | 20–28% | 24% | 25% | 25% | 24% | 24% |
| Release profile: | | | | | | |
| 1st hour | 20–40% | 29% | 30% | 29% | 29% | 30% |
| 8th hour | 55–75% | 71% | 71% | 71% | 72% | 71% |
| 16th hour | >75% | 89% | 90% | 90% | 89% | 89% |

EXAMPLE 4

Plasma concentrations "in vivo" following administration of a single dose of the product of Experiment 1 were determined: A hard gelatin capsule containing about 310 mg of microgranules, corresponding to about 75 mg of ambroxol hydrochloride, of the product of Experiment 1 of Example 1, was administered at once to each of 12 healthy human volunteers, in order to determine the resulting plasma levels of the active ingredient.

The following Table III individual results of concentrations were obtained (results as ambroxol, $\mu$g/ml):

TABLE III

| Subjects No. | \multicolumn{10}{c}{Time after single dose administration (in hours)} | | | | | | | | | |
|---|---|---|---|---|---|---|---|---|---|
| | 00 | 01 | 02 | 04 | 08 | 012 | 16 | 24 | 32 | 36 |
| 01 | 0.0 | 16.4 | 110.6 | 175.1 | 145.1 | 100.4 | 60.1 | 34.7 | 29.4 | 16.1 |
| 04 | 0.0 | 17.0 | 121.9 | 122.8 | 103.5 | 85.3 | 55.3 | 49.7 | 33.0 | 18.4 |
| 05 | 0.0 | 25.2 | 155.1 | 229.1 | 160.4 | 110.8 | 70.4 | 66.0 | 56.4 | N.D. |
| 06 | 0.0 | 12.1 | 92.0 | 191.4 | 138.9 | 118.8 | 71.5 | 65.1 | 62.2 | 21.4 |
| 07 | 0.0 | N.D. | 86.6 | 167.2 | 124.7 | 100.0 | 48.2 | 37.7 | 29.5 | N.D. |
| 08 | 0.0 | 12.8 | 100.5 | 242.7 | 153.7 | 97.5 | 54.1 | 41.9 | 44.7 | 20.4 |
| 09 | 0.0 | 31.6 | 87.2 | 182.1 | 127.8 | 114.3 | 82.8 | 50.8 | 43.8 | 18.3 |
| 10 | 0.0 | 23.8 | 137.4 | 158.7 | 110.3 | 91.9 | 50.9 | 43.3 | 37.8 | N.D. |
| 11 | 0.0 | 18.7 | 140.0 | 160.2 | 130.1 | 80.2 | 69.4 | 33.9 | 23.7 | N.D. |
| 12 | 0.0 | 20.8 | 111.6 | 139.4 | 116.0 | 77.7 | 73.7 | 61.2 | 50.1 | 33.4 |
| M | 0.0 | 16.9 | 112.4 | 166.3 | 126.6 | 92.9 | 61.0 | 47.0 | 38.7 | 12.1 |
| S.D. | 0.0 | 8.04 | 26.12 | 41.86 | 20.52 | 16.30 | 11.02 | 11.49 | 10.46 | 11.58 |
| S.E. | (+/−) | 0.02.32 | 7.26 | 12.08 | 6.92 | 4.70 | 3.18 | 3.31 | 3.01 | 3.34 |

M = Mean
SD = Standard Deviation
SE (+/−) = Standard Error

The pharmacokinetic data obtained were satisfactory and confirmed the efficacy of the product of the Experiment 1 of Example 1.

The pharmacokinetic parameters reported in Table IV below were obtained:

TABLE IV

| Parameter | Values Obtained |
|---|---|
| AUC 0–24 ($\mu$g/hour/ml$^{-1}$) | 2,815.42 |
| Ke (hour$^{-1}$) | 0.1038 |
| T max (hour) | 4.15 |
| C max (hour) | 1,564.36 |
| t ½ α phase (hour) | 2.77 |
| t ½ β phase (hour) | 14.41 |

BRIEF DESCRIPTION OF THE DRAWING

The accompanying FIGURE of Drawing is a graph of the mean plasma concentrations of ambroxol hydrochloride following administration of a single dose thereof to 12 healthy volunteers, of hard gelatin capsule containing programmed-release microgranules that included 75 mg of ambroxol hydrochloride, prepared in Experiment 1 of Example 1.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A programmed-release ambroxol·HCl pharmaceutical dosage form, comprising a plurality of inert core microgranules of a variety of particle sizes ranging from 0.3 to 1.2 mm, said inert core microgranules being coated with multiple alternating microlayers of (1) micronized ambroxol hydrochloride active agent and (2) delayed-release film material, said coated microgranules including an external microlayer of delayed-release film material, and said coated microgranules having particle sizes ranging from 0.6 to 1.5 mm.

2. The programmed-release dosage form as defined by claim 1, comprising from 100 to 500 mg of micronized ambroxol hydrochloride per g of said inert core microgranules.

3. The programmed-release dosage form as defined by claim 1, said inert core microgranules comprising sugar and starch.

4. The programmed-release dosage form as defined by claim 1, said multiple alternate microlayers of delayed-release film material comprising a polyvinylpyrrolidone, shellac or polyvinylpyrrolidone/shellac admixture.

5. The programmed-release dosage form as defined by claim 1, said external microlayer of delayed-release film material comprising shellac, an acrylic polymer, hydroxypropyl cellulose, ethyl cellulose, or mixture thereof.

6. The programmed-release dosage form a defined by claim 1, comprising a unitary dosage amount thereof, confined within a hard gelatin capsule.

7. The programmed-release dosage form as defined by claim 1, said multiple alternate microlayers of micronized ambroxol hydrochloride further comprising talc, an aluminum or magnesium silicate, lactose or starch.

8. The programmed-release dosage form as defined by claim 1, adopted to deliver the ambroxol hydrochloride content thereof, in vivo, according to the following release-rate profile:

| 1st hour | 20% to 40% |
|---|---|
| 8th hour | 55% to 75% |
| 16th hour | >75%. |

9. The programmed-release dosage form as defined by claim 1, adopted to deliver the ambroxol hydrochloride content thereof, in vivo, as to maintain a therapeutically effective plasma level thereof for about 24 hours.

10. The programmed-release dosage form as defined by claim 1, said external microlayer being devoid of said micronized ambroxol hydrochloride active agent.

11. A process for the production of the programmed-release dosage form as defined by claim 1, comprising (a) providing a plurality of inert core microgranules of a variety of particle sizes ranging from 0.3 to 1.2 mm, (b) providing a therapeutically effective amount of micronized ambroxol hydrochloride, (c) applying on said inert core microgranules multiple alternating microlayers of said micronized ambroxol hydrochloride and of a solvent solution of a delayed-release film-coating material, wherein said delayed-release film-coating material is external to said micronized ambroxol hydrochloride, and (d) consolidating each microlayer to dryness.

12. The process as defined by claim 11, said solvent solution comprising an aqueous or organic solution, or mixture thereof.

13. A process for eliciting an expectorant response in a mammalian organism in need of such treatment, comprising administering to such organism a therapeutically effective amount of the programmed-release dosage form as defined by claim 1.

* * * * *